United States Patent [19]

Zeiser

[11] Patent Number: 4,608,016
[45] Date of Patent: Aug. 26, 1986

[54] DENTAL MODEL IN CONJUNCTION WITH A BASE PLATE FOR MAKING A DENTAL MODEL

[76] Inventor: Manfred Zeiser, 7141 Schwieberdingen, Fed. Rep. of Germany

[21] Appl. No.: 571,516

[22] Filed: Jan. 17, 1984

[30] Foreign Application Priority Data

Jan. 19, 1983 [DE] Fed. Rep. of Germany ....... 3301615
May 27, 1983 [DE] Fed. Rep. of Germany ....... 3319263
Jun. 3, 1983 [DE] Fed. Rep. of Germany ....... 3320050

[51] Int. Cl.⁴ .................................................. A61C 19/00
[52] U.S. Cl. .......................................... 433/74; 433/60
[58] Field of Search ........................... 433/74, 34, 60

[56] References Cited

U.S. PATENT DOCUMENTS

| | | | |
|---|---|---|---|
| 2,619,725 | 12/1952 | Roeser | 433/60 |
| 2,700,219 | 1/1955 | Lindley | 433/60 |
| 2,911,722 | 11/1959 | Benfield et al. | 433/60 |
| 3,581,398 | 6/1971 | Thomas | 433/74 |
| 3,702,027 | 11/1972 | Marshall | 433/34 |
| 4,021,916 | 5/1977 | Spalten | 433/74 |
| 4,059,902 | 11/1977 | Shiokawa | 433/34 |
| 4,242,812 | 1/1981 | Randoll et al. | 433/74 |
| 4,283,173 | 8/1981 | Browne | 433/34 |
| 4,439,151 | 3/1984 | Whelan | 433/74 |

Primary Examiner—John J. Wilson
Attorney, Agent, or Firm—Michael J. Striker

[57] ABSTRACT

A dental model has a tooth stump which is releasably secured on a stable base plate made of synthetic plastic material. The base plate is formed with a ridge and a side wall projected upwardly from the base plate and formed integrally therewith. The base plate further has a perforation which together with the surfaces forming the ridge and the side wall constitute guiding elements for the tooth stump, these guiding elements producing during the hardening of the model material, guiding surfaces on the tooth stump.

45 Claims, 15 Drawing Figures

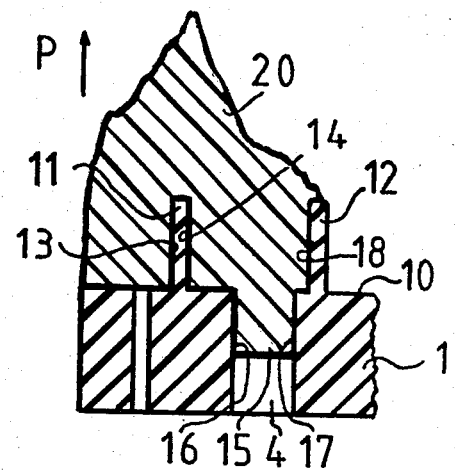
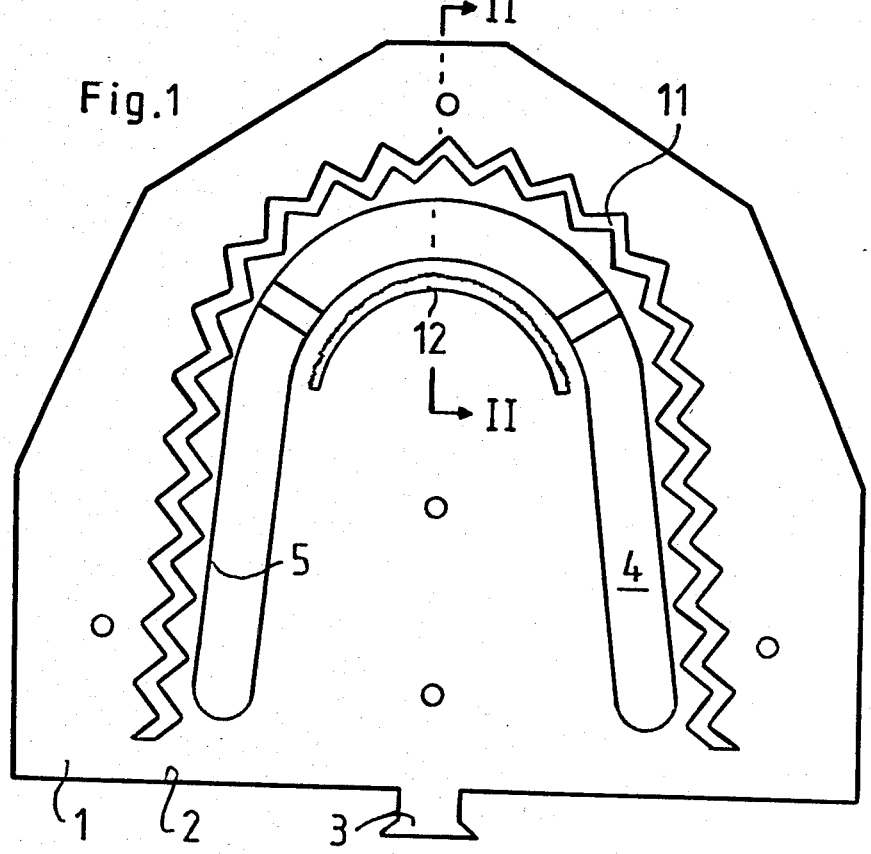

DENTAL MODEL IN CONJUNCTION WITH A BASE PLATE FOR MAKING A DENTAL MODEL

BACKGROUND OF THE INVENTION

The present invention relates to a device for making a dental model.

One of conventional methods of manufacturing dental models is described in German patent P No. 2949697. In this method a positive impression of the teeth made out of model material and having tooth stumps is releasably fastened to a prefabricated solid base plate formed of formstable plastics. Individual openings are made in the base plate which operate as guide elements for pins which are inserted into hardenable model material and rigidly and unreleasably anchored in the tooth stump. This method has been widely utilized in practice at the present time to produce dental models with precision which has not been obtained earlier. However, manufacturing of these guide elements, namely bores and dowel pins has been time-consuming. Furthermore, individual fixation of positions of the pins has been also time-consuming.

A dental keying device for a dental model is described in U.S. Pat. No. 3,581,398. In this device a guiding ridge for guiding the dental model is utilized in place of individual pins. This ridge is however unreleasably anchored in the model and detachably made on the base plate, which model is only partially formed of hardenable material and is composed not only of the prefabricated base plate. Thereby no guiding surfaces are produced on the tooth stumps during the hardening of the model material. Furthermore, the known dental keying device has no perforations which would provide a simple and reliable orientation of the base plate relative to the dental cast.

SUMMARY OF THE INVENTION

It is an object of the present invention to provide a combination of the dental model with a formstable prefabricated base plate, which is economical and time-saving.

This and other objects of the invention are attained by a dental device for making teeth prothesis portions, such as cast fillings, crowns, bridges, dental protheses or the like, which in combination comprises a prefabricated base plate; a dental positive tooth impression having tooth stumps and made of a hardenable model material, said tooth stumps being releasably securable on said base plate; and guide means for guiding at least one tooth stump on said base plate, said guide means including at least one guiding wall portion formed on said base plate integrally therewith, said wall portion producing respective guiding surfaces on said tooth stump during the hardening of the material of said tooth stumps when the base plate is set on the tooth impression.

The invention is based on the recognition that the guidance between the wall portion rigidly formed on the base plate and the corresponding guiding surfaces on the dental model is possible when the model is formed of model plastics because usually utilized plastics on the epoxy-basis are abrasion-resistant. Individual tooth stumps can be therefore reset on the base plate many times without fear that an increasing play may be formed between the wall portion on the base plate and the guiding surfaces on the tooth stump. As compared to known methods of making dental models, in which dowel pins have been used, the guidance of the tooth pump on the base plate is substantially improved due to the extension of flat surfaces cooperating with each other.

According to one of the concepts of the invention the base plate may be formed with a perforation having side walls, the side walls of said perforation constituting said guiding wall portion and producing said guiding surfaces on said tooth stump. These side walls of the perforation extending through the base plate form the wall portion which is especially stable. The manufacturing of such a perforation is very simple and the perforation which serves as a guide element provides for a precise positioning of the base plate on the dental cast filled with a synthetic plastic material, which cast is so oriented that the perforation and the tooth arch coinside with each other.

According to a further modification of the invention the base plate may have a base surface and be formed with a ridge extended outwardly from said base surface and being integral with said base plate, said ridge following the dental arch and being inserted into said impression approximately centrally of a tooth stump, said ridge forming a further wall portion which produces further guiding surfaces on the tooth stump. In this modification it should be taken into account that the tooth stump is not always precisely guided in the region of chewing surfaces. Tests have shown that with a very small number of the base plates provided with the ridges and perforations of various shapes any models, which in practice would correspond to the jaw shapes, could be manufactured. In this embodiment the tooth stump is guided only centrally over the relatively short portion. Also when the ridge is very stable and relatively thick a certain tilting movement of the tooth stump can not be totally avoided in practice, which could lead to some inaccuracies during the formation of the tooth seat portions. This tilting movement occurs particularly with narrow tooth stumps in the region of front teeth.

As has been known from experience, epoxy-based plastics can provide for precise dimensions in the dental models, and these plastics have insignificant shrinking properties, thereby the tooth stump produced from such plastics can be guided over the base plate many times. There are regions of the tooth stump, fixed between two or more guiding surfaces which are perpendicular to the base plate.

The base plate may further include at least one lateral projection outwardly extended therefrom and at a distance from said ridge, said projection having an inner face perpendicular to said base plate and being integral with the base plate, said projection also forming said guiding surfaces on said tooth stump during hardening of the model material.

It is particularly advantageous when the perforation is formed on the palate side of the base plate and the ridge is formed on the lip side of that plate. The ridge and the perforation can extend over the entire tooth arch whereas the additional projection can extend only over the region of the front teeth. The member of cooperating guiding surfaces is substantially increased as compared to known constructions with dowel pins so that a very precise guidance of the tooth stump over the base plate is warranted.

According to a further modification of the invention two projections may be formed on the base plate, said two projections being formed at two opposite sides of the ridge. One of said projections may be partially interrupted by slots to form wall portions spaced from each other in the direction of the tooth arch, said wall portions forming at least some of said guiding surfaces. These slots are open towards the edge of the base plate and thus form passages through which air inclusions and excessive model material can escape. These slots form further guiding means for guiding the tooth stump relative to the base plate.

The one or two projections forming the wall portions may be formed with protrusions engageable in respective recesses formed in the tooth stump.

At least one projection may have an inner surface and provided with a plurality of guiding grooves in said inner surface, said projection further having an upper surface and being provided with a plurality of guiding notches in said upper surface, said guiding grooves merging into said guiding notches.

The base plate of the dental making device according to the invention can be manufactured by direct injection into the mold of synthetic plastic material. A commercially available plastics known under trademark HOSTAFORM, which has good sliding properties, may be utilized. Thereby the base plate can be made thinner than usual and the wall portions thereof contribute to the rigidity of the base plate.

The base plate may be provided with a bottom plate which closes said perforation from beneath. Thus no material can penetrate through the perforation in the upward direction during the manufacturing of the model.

The bottom plate may have abutments extended into said perforation, the cross-section of said abutments corresponding to the cross-section of said perforation. The bottom plate can be connected to the base plate either in a force-locking fashion or in a form-locking fashion. The height of the abutments can influence the height of the guiding surfaces on the tooth stump.

The base plate can have such a periphery that would correspond to the dental arch. To reduce costs of manufacturing of the base plate a quandrant-shaped periphery of the base plate is herein suggested so that the plate is adjusted to only one half of the dental arch. The base plate may have one base surface and a further base surface opposite to the aforementioned base surface, said first wall portion and said further wall portion formed by the ridge both extending from said aforementioned base surface and said further base surface, The ridge then can serve for securing the base plate in the articulator. The base plate has in this embodiment a mirror-inverted construction because the aforementioned first base surface and the further base surface are parallel to and symmetrical relative to a central plane at the base plate. With such a base plate the model can be also secured on the back side of the plate whereby the left-hand half of the dental arch can be fixed to one side of the base plate and the right-hand half of the dental arch can be fixed to another side of the base plate. Only one base plate is therefore required for a complete two-part dental arch.

It is particularly advantageous to utilize such plastics as epoxy or epimin plastics for a model material. Such plastics are known under trademarks ARALDIT or IMPREDUR. These plastics have neutral dimension qualities and do not expand while they are cured, which is very important for the precision of the model manufacturing.

Dental models can be also produced of super hardenable gypsum known in the art. It is to be taken into consideration, when this material is used, it is brittle in the dry state. If the tooth stump formed of hardenable gypsum were not precisely set in the initial position on the ridge of the base plate, the width of which is not constant over its entire length due to unavoidable manufacturing allowances, the tooth stump could break because of wedge action of the ridge. This problem does not occur with the above mentioned plastics because those plastics after hardening have a certain elasticity.

According to a still further embodiment of the invention the tooth stump may be provided with a reinforment unreleasably imbedded therein, said reinforcement surrounding said ridge at two lateral sides thereof, said reinforcement including a slide with two arms which engage said ridge and a projection extended outwardly from said arms, said slide having an outer surface which is knurled. The wedge forces exerted on the ridge are thus taken up by that reinforcement whereby the ridge is deformed as the tooth stump.

According to a further modification of the invention the base plate has a lip-oriented outer side and a palate-oriented inner side, said ridge being formed at the lip-oriented side relative to said perforation and said projection being formed at the palate-oriented side relative to said projection.

Furthermore, the side walls forming said perforation may be at least partially toothed.

The ridge forming said further wall portion may be at least partially toothed, and the projection forming the additional guiding wall portion may be also toothed at one side thereof.

The ridge may have a cross-section which is gradually decreased towards said tooth stump.

The base plate may be formed with a plurality of bores in the region of said ridge and further include pushers insertable into said bores from the side of the base plate facing away from the tooth impression, said pushers pushing the tooth impression out from said guiding wall portion. The pushers may be threaded pins which also serve for fixing the tooth stump to the base plate.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 is a top plan view of the base plate;

FIG. 2 is a sectional view along line II—II of FIG. 1;

DETAILED DESCRIPTION OF THE PREFERRED EMBODIMENTS

Figure 4:
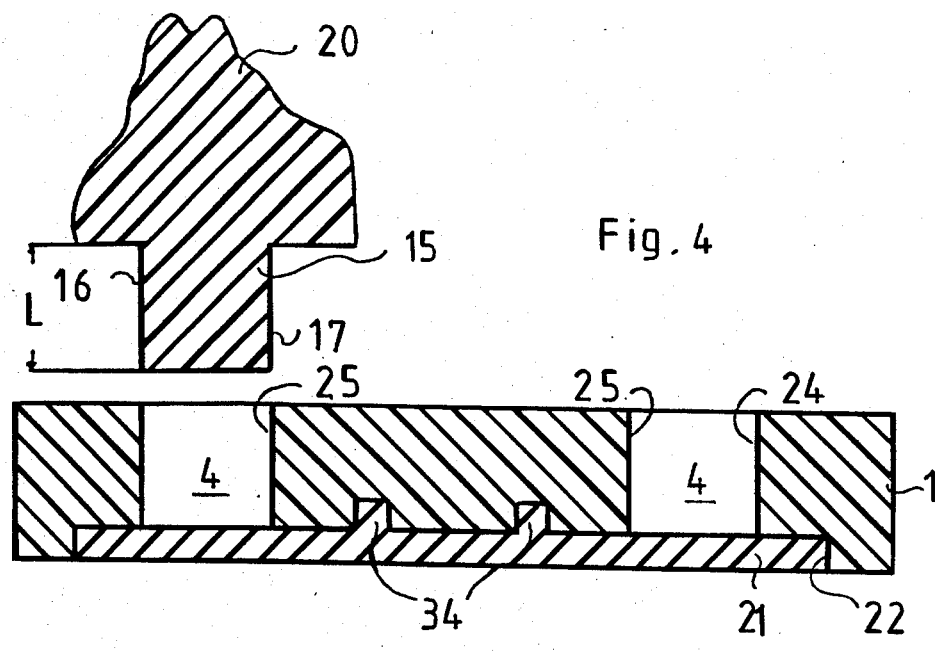
FIG. 4 is a sectional view taken along line IV—IV of FIG. 3.

Referring now to the drawings in detail, and firstly to FIGS. 1 and 2, it will be seen that in this preferred embodiment of the invention a base plate 1 has a substantially polygonal periphery which closely corresponds to the shape of the dental model. The base plate 1 is a one-piece member manufactured by injection molding from a form-stable plastics. An abutment or extension 3 projects outwardly from the side surface 2 of the base plate, for securing the base plate in a tool.

Base plate 1 has an opening or perforation 4 having a contour of the tooth arch. Wall portions 5 that form perforation 4 extend parallel to each other and perpendicular to the base plate 1, these wall portions serving as a guide element for a dental model.

A web or ridge 11 projects upwardly from and perpendicularly to the upper base surface 10 of the base plate, ridge 11 being tooth and altogether with the base plate has a contour of the toothed segment and on the lip side is enclosed at the perforation 4. This ridge 11 is formed integrally with the base plate and is unreleasably connected thereto. Although this ridge is relatively thin it must be rigid and form-stable because it serves as a guiding element. On the palate side opposite to perforation 4 and at a distance from ridge 11 is formed a side wall or projection 12 integrally formed with base plate 11 and extended normally thereto. This side wall also serves a a guiding element.

It is essential for the present invention that the above-described guiding elements form on the tooth stump 20 respective guiding surfaces during the hardening of the dental model material. Thus guiding surfaces 13 and 14 at both lateral sides of ridge 11 result in the tooth stump 20. The model material flows also into the perforation 4 and forms there a projection 15 with two parallel guiding surfaces 16 and 17. Finally, the inner surface of side wall or projection 12 forms a guiding surface 18 in the tooth stump 20.

The dental model according to the invention is produced as follows:

The premanufactured base plate 1 is clamped by means of guiding projection or abutment 3 in a tool. Then the cast spoon with the dental impression is so oriented and fixed that the ridge 11 indicates approximately the center of the cast. The cast is then filled with a model material. Furthermore, the model material is applied onto the ridge 11 and side wall 12. Then the base plate is displaced parallel to and against the cast. Thereby the model material can not flow away at undesired spots, which is recommended in order to place a collar, preferably of wax, around the cast. Practice has shown that if a synthetic plastic is utilized as the model material the base plate must be first set out on the cast when this synthetic plastic changes over from the flowable or liquid state into the sticky or adhesive state.

After hardening of the model material the tooth stump 20 can be easily pulled out from the base plate 1 in the direction of arrow P. After working of the tooth stump 20 the latter can be again placed back into its initial position on the base plate whereby the tooth stump will be readjusted on the upper surface 10 of the base plate 1. Inasmuch as ridge 11 has a non-uniform shape the initial position of tooth stump is accurately reproducible.

Figure 3:
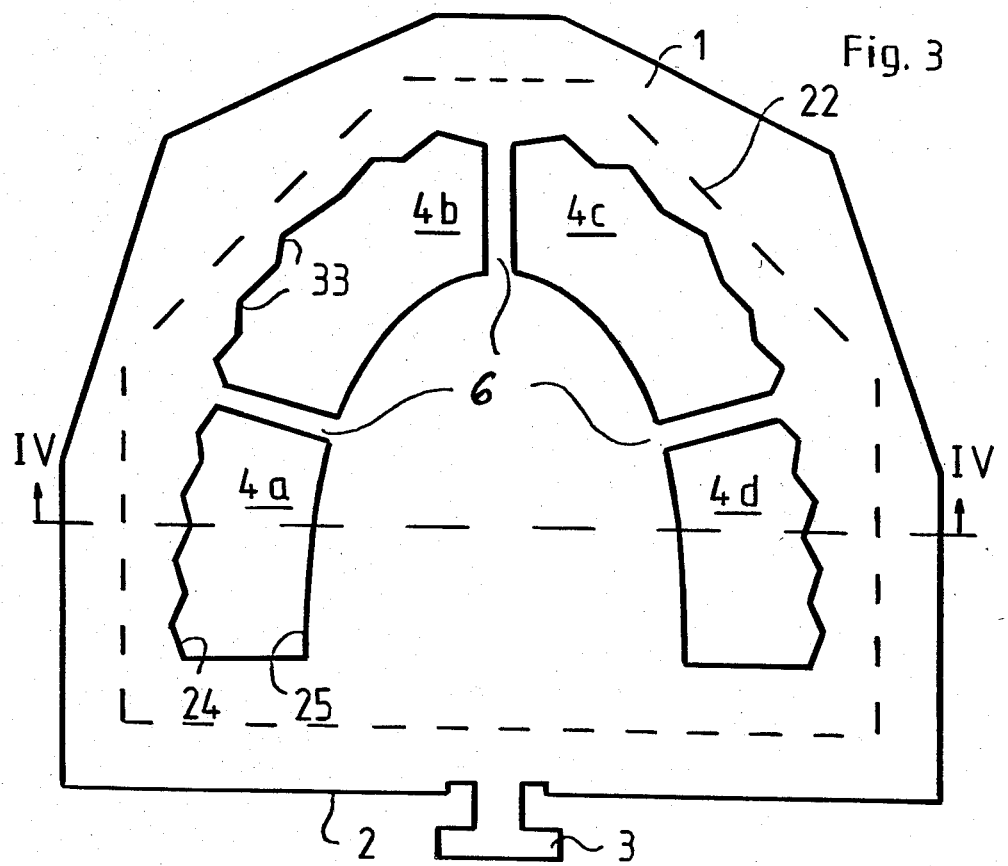
FIG. 3 is a top plan view of another embodiment of the base plate.

FIGS. 3 and 4 show a modified embodiment of the invention, in which only the perforations are provided in the base plate 1 without, however the provision of the outwardly projected ridge or side wall of the embodiment of FIGS. 1 and 2. The perforation 4, which as a whole has a contour of the tooth segment is subdivided into individual, shaped chambers 4a, 4b, 4c and 4d by transversally extended ribs 6. Reference character 21 denotes a bottom plate which is inserted in a respective recess 22 provided in the bottom of the base plate and has a smaller peripheral size than that of the base plate 1. Bottom plate 21 is secured in recess 22 by any suitable means and closes the chambers 4a to 4d of the perforation from beneath. Base plate 1 and bottom plate 21 altogether practically form a two-part form for forming the guiding surfaces on the tooth stump.

For producing a dental model the base plate 1 is placed over the model cast filled with a model material, preferably eposy plastics; the cast is then so oriented in the tool that it registers with the tooth archs and perforation 4. This orientation or alignment is so simple because the dental cast can bear against the perforation 4. Thereafter the perforation 4 is closed with bottom plate 21 and the base plate 1 is pressed against the cast. Thereby the plastics flows into the perforation so that after the hardening of the plastics form-stable guiding surfaces 16 and 17 are formed on a projection 15 formed on the tooth stump. This guiding projection 15 is formed by chamber 4a; in other words this guiding projection 15 can be accurately inserted into this form chamber. Length or height "L" of this guiding projection 15 corresponds to the depth of base plate 1 minus the thickness of bottom plate 21. Opposite side walls 24 and 25 forming perforation 4 or shaped chambers 4a–4d constitute a guiding element for guiding projection 15 in this embodiment of the invention. Thereby the orientation of the dental cast relative to the base plate 1 is automatically ensured and guiding surfaces 16 and 17 are aligned with the center of the toothed segment or these surfaces extend symmetrically relative to that center. The guiding elements formed in the base plate are particularly form-stable. Outer walls of chambers 4a through 4d are toothed.

Figure 5:
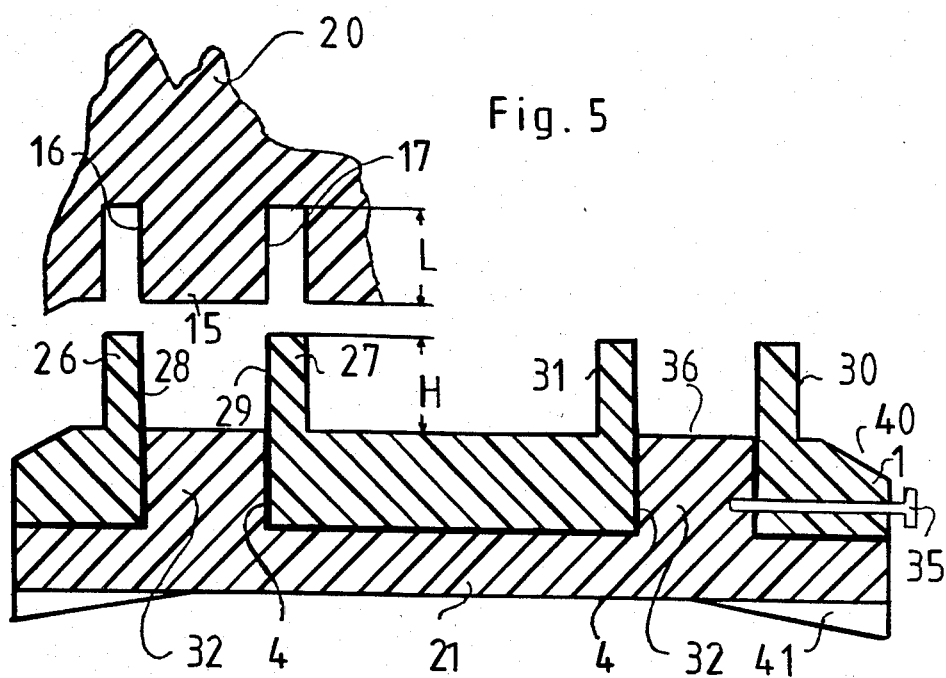
FIG. 5 is a sectional view similar to FIG. 4, but of a further embodiment of the invention.

In the embodiment illustrated in FIG. 5, a ridge 26 or 27 is formed as an extension of the side wall 24 or 25 of perforation 4, ridges 26 and 27 being formed integrally with base plate 1. At least inner walls 28, 29 of these ridges are utilized supplementarily for guiding the tooth stump 20. Outer surfaces 30, 31, can also be used for guiding the tooth stump. If length or height "L" of guiding projection 15 corresponds to the height "H" of the ridges, then the extension or abutment 32 provided on the bottom plate 21 projects into and fills the perforation 4 or individual form chambers 4a–4d shown in FIG. 3. The shape of the cross-section of extension 32 also corresponds to the cross-section of perforation 4 and the height of this extension corresponds to the thickness of base plate 1. It is therefore understood that if the height of extension 32 is smaller than the thickness of base plate 1 this extension only partially fills perforation 4 so that the opposite side walls of the respective ridge as well as the side walls of the perforation are only partially used for guiding the tooth stump.

Some individual advantageous modifications can be afforded in the embodiments according to FIGS. 3 to 5. In the embodiment of FIG. 3 the wall 24 of the perforation 4 on the lip side is toothed as mentioned above; this wall can be also provided with grooves 33 and respective projections. These grooves alternating with the projections extend normally to the base plate 1 and serve to enable the tooth stump, which would be later sucked out from the model, to be again set on the base plate. Naturally, the palate side wall 25 which is opposite to side wall 24 of perforation 4 can be provided with retention means. All the guiding wall portions extend perpendicularly to the base plate 1. Outer walls 30 and 31 of the ridges can also be inclined to the base plate whereby the base plate molded from the plastics, preferably a glass-fiber-reinforced polyamide, can be easier released from the tool. Ridges 26 and 27 can be also toothed.

In the embodiment of FIG. 4, bottom plate 21 is connected to the base plate 1 in a force-locking fashion. Therefore arresting projections or abutments 34, are engaged in respective recesses formed in the base plate.

In the embodiment of FIG. 5, the bottom plate 21 is connected to base plate 1 in a form-locking fashion by means of pins 35. One can use threaded pins which are inserted into extension 32 from the side wall of base plate 1. In the modification of FIG. 5 the periphery of the bottom plate 21 corresponds to that of the base plate.

Base plate 1 is formed by injection molding as a one piece of a thermoplastic material, preferably of a commercially available synthetic plastic material known under the trademark HOSTAFORM. This material can be also utilized for manufacturing bottom plate 21. The bottom plate, however, can be made of metal. The essential point is that free upper face 36 of extension 32 or the region of the bottom plate enclosing the perforation 4 should have a very clean and smooth surface so that individual tooth stumps would be received in their initial position on the base plate after readjusting. This free upper face 36 must be polished. The bottom plate can be also made out of glass.

As seen from FIG. 5 the base plate 1 at the edge thereof is tapered in the direction towards the ridges as shown by reference character 40. Thereby air inflows in the model material can escape; the ridge should not necessarily entirely surround the perforation but can have a slot which would extend normally to the elongation of the ridge. Bottom plate 21 can also have chipcast ribs 41. Furthermore, means for securing the base plate in an articulator may be provided, these means are not shown herein. Finally, in the above-described embodiments, a portion of the tooth segment can be pressed out from the rear side of the socket plate through the perforation over the length of the base plate, and the bottom plate is then removed. This is especially desired with large wax models of the teeth stumps.

Figure 6:
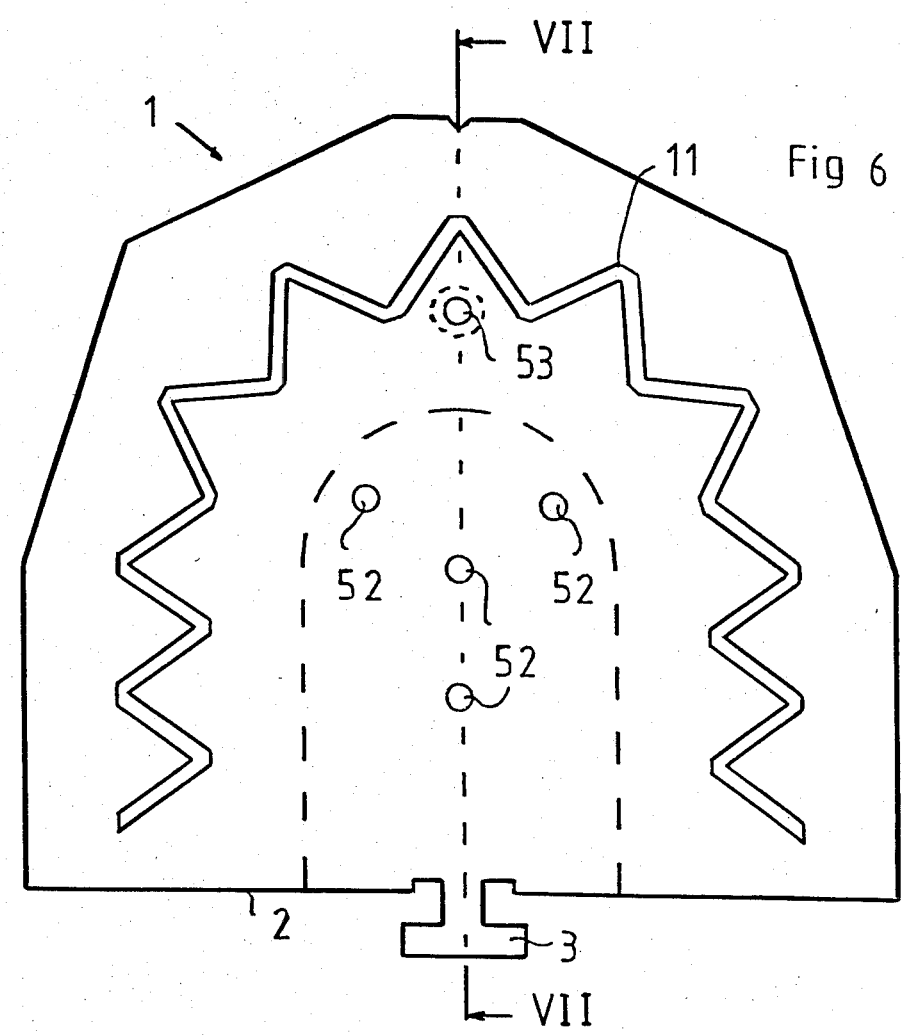
FIG. 6 is a top plan view of the base plate of yet another embodiment.
Figure 10:
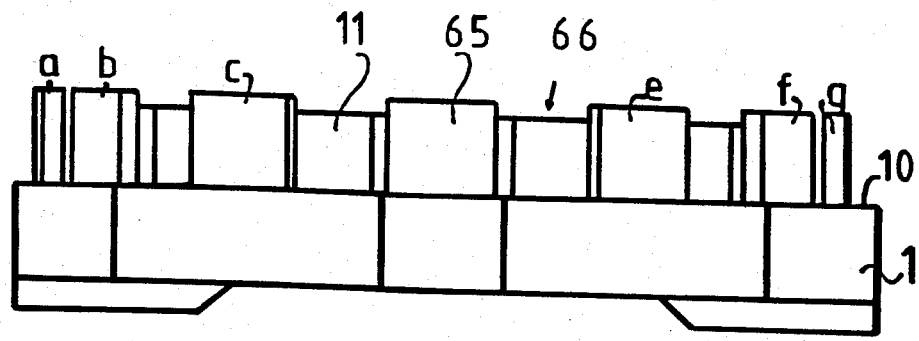
FIG. 10 is a front view of the base plate of FIG. 9.

FIG. 6 illustrates still another embodiment of the invention. Base plate 1 has no perforation but is formed with a ridge 11 which has a zigzag configuration. Ridge 11 formed integrally with base plate 1 projects upwardly from the upper face of the base plate. A horseshoe-shaped recess 50 is provided in the bottom side 51 of the solid base plate 1. A number of through bores 52 are further formed in the region of recess 50. Furthermore, a funnel-shaped bore 53 is further provided in the base plate; excessive model material can escape through that bore. And vice versa, the model material can be filled in by an injector through bore 53 so that an unobjectionable formation of the cast without air inflows is warranted.

Figure 8:
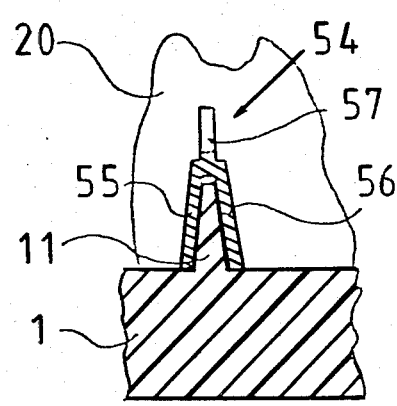
FIG. 8 is a partial sectional view illustrating still another modification of the invention.
Figure 7:
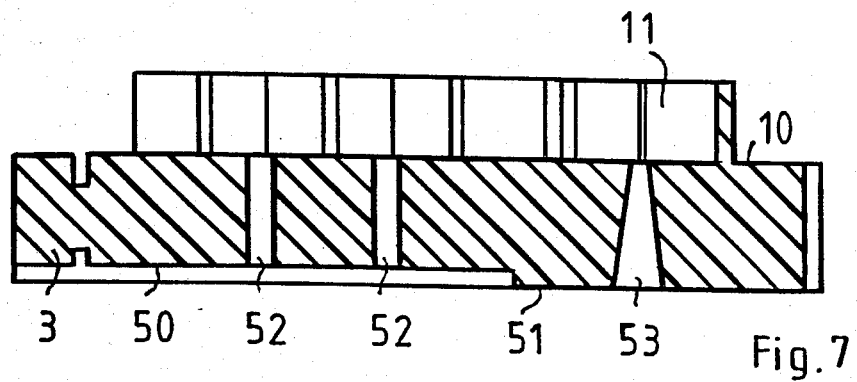
FIG. 7 is a sectional view taken along line VII—VII of FIG. 6.

FIG. 8 shows a partial sectional view through the dental model which is manufactured of hardening gypsum. An unreleasable reinforcement 54 is embedded in the tooth stump 20, this reinforcement lies on two opposite sides of the ridge 11. Reinforcement 54 is comprised of a slide with two lateral arms 55 and 56 which merge into a projection 57. The upper surface of the slide knurled or beaded so that a rigid, non-loosable connection of the slide with the tooth stump is ensured. The position of the slide is secured in the known fashion near the dental cast by means of a homing device. Thereby, one direction needle points to the cast and another direction needle points to the ridge of the base plate. The slide after such a positioning is clamped on the ridge 11.

It is understood that some other modifications not shown in the drawings are possible in this invention. For example, ridge 11 can be wave-shaped, although straight portions of the ridge are preferable to enable the slide 54 to easily pass onto the ridge. The ridge can also have spherical side surfaces. The height of the ridge can vary over the length of the ridge; it should be noted that all disturbing portions of the ridge can be removed by a milling tool. Retensions can be impressed by heat-deforming on the teeth-free portion of the base plate. Furthermore, a number of parallel ridge-like projections can be formed on the base plate, of which the projections which are not necessary, can be further removed. The base plate is universally usable and it does not require additional working steps.

The drawing shows the parts of the dental model on enlarged scale. The thickness of the base plate is about 10 mm and the height of ridge 11 with the lowermost distance of the ridge from the cast of about 6 mm must be about 1 mm. With the base plates having a perforation the thickness of the base plate can be reduced to 5 mm due to extended guiding surfaces.

In the embodiment shown in FIGS. 9 to 12 a side wall 62 is formed at the distance from ridge 11, which wall is integrally made with the base plate 1 and has an inner surface extended perpendicularly to the base plate 1. The wall 62 is formed on the palate side of the model while a second side wall 65 is provided on the lip side of the base plate. Slots 66 are made in the wall 65 to form individual wall portions 65a to 65g. An inner surface 67 of each wall 65a to 65g projects upwardly from and perpendicularly to the upper face 10 of base plate 1. Outer faces of wall 62 and wall 65 can be inclined to the base plate 1 whereby the base plate can without any difficulties be released from the tool.

Figure 12:
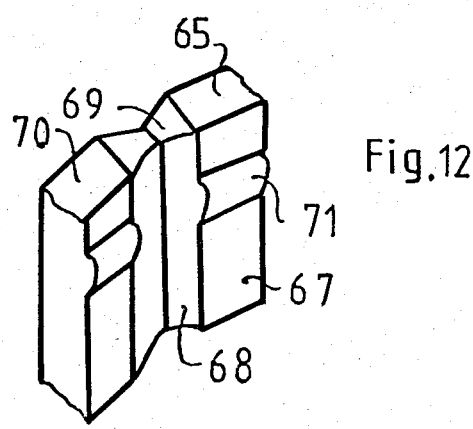
FIG. 12 is a perspective view of a portion of the side wall.

With reference to FIG. 12 it will be seen that the outer side wall or projection 65 can have at the inner face thereof individual guide notches 68 which merge into guide groove 69 formed in the upper face 70 of wall 65 interrupted by slots 66 as mentioned above. Furthermore, wall portions 65a–65g can have at the inner faces 67 thereof parallel protrusions or beads 71 which are engaged in recesses 85 for locking individual tooth stumps on the base plate 1.

Figure 9:
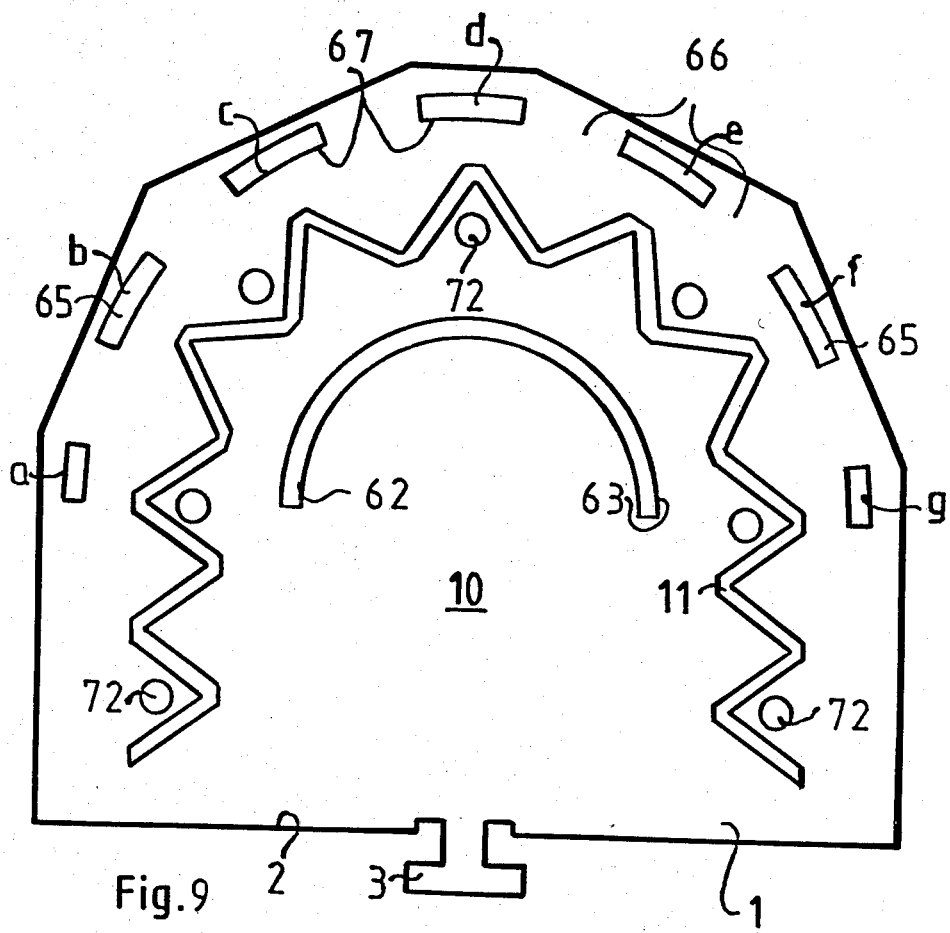
FIG. 9 is a top plan view of the base plate of yet further modification.
Figure 11:
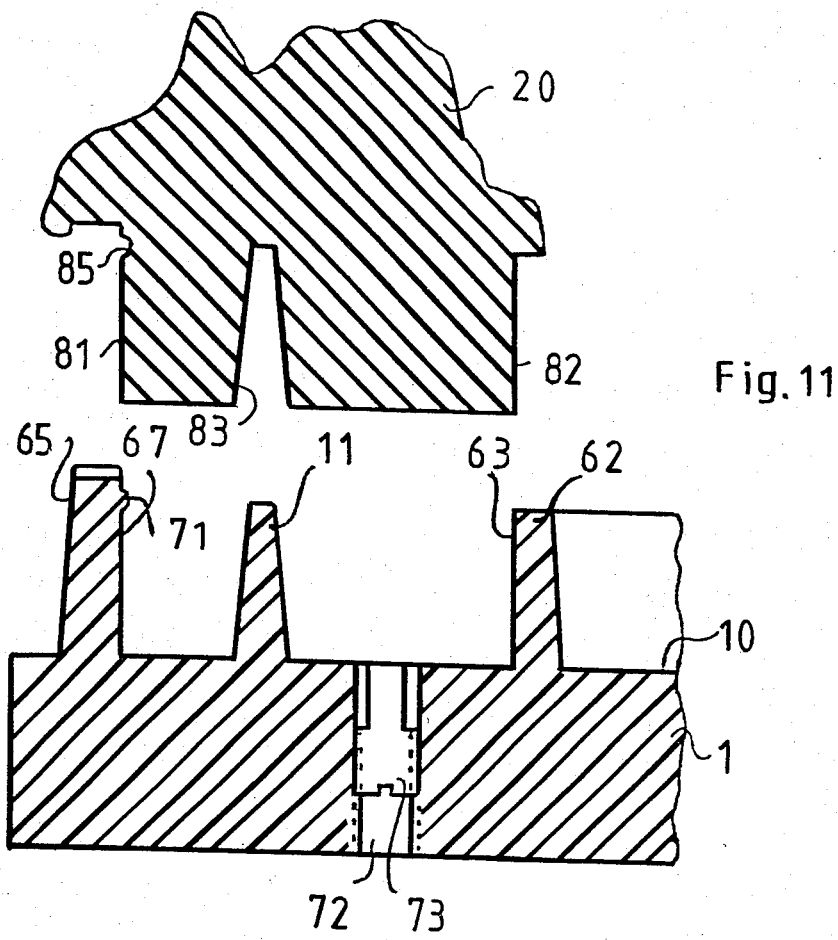
FIG. 11 is a partial section through the base plate of FIG. 9 in conjunction with a respective teeth stump in section.

As shown in FIGS. 9 and 11 base plate 1 in the vicinity of ridge 11 has a number of through bores 72 in which threaded pins 73 are inserted as ejectors or pushers. The dental cast is filled with the epoxy material up to the height which corresponds to the supporting height of the base plate. The epoxy material is also applied onto the base plate in the region of ridge 11 and between the side walls 62 and 65. The base plate 1 is then set on the dental cast so that the ridge points somewhat centrally of the cast. Thereby material excess and air inclusions can escape through the slots outside of the side wall. The epoxy material flows thereby between these side portions 65a to 65g so that an additional guide is produced. After the hardening of the model material the model can be lifted from the base plate and decomposed into individual tooth stumps.

FIG. 11 illustrates a sectional view through an individual tooth stump. This tooth stump has two parallel peripheral surfaces 81, 82 which are normal to the base plate and a groove 83 the cross-section of which corresponds to the cross-section of ridge 11. Furthermore, a notch or recess 85 is formed in this tooth stump the cross-section of which corresponds to that of projection 71. During resetting of the tooth stumps inner surfaces of side walls 62 and 65 serve as a guide and a necessary press fit of the tooth stump in the final position is ensured because this tooth stump is continuously fixed between several wall portions. The tilting movement of the tooth stump is efficiently prevented by the side walls 62 and 65. During the resetting of the tooth stump the outer wall portions 65a–65g yield outwardly in a spring-elastic fashion unless the projection 71 becomes engaged in recess 85. This pivoting movement of the side wall 65 is possible due to the elasticity of plastics material of the base plate and owing to slots 66. This manner of securing the tooth stump to the base plate is possible with models of plastics because they are non-abrasive. When gypsum models are utilized one must take into consideration breaks or eruptions. Naturally any deviations from the above-described process are possible, however within the limits of this invention. The base plate, for example can have only one side wall or projection either on the palate side or on the lip side. Guide notches or guide grooves can be provided on the palate side of the wall 62 or 65. The side wall could have an extension in the circumferential direction, which would correspond to ridge 11. The tooth stumps are in the region of the jaw teeth so wide that a sufficient guide can be ensured solely by the ridge.

The initial lifting of the dental model made out of plastics from the base plate presents a number of considerable difficulties. In order to facilitate this initial separation or lifting of the model threaded pins 73 are guided in bores 72. These pins are smoothly screwed into the base plate from the side thereof facing away from tooth stump 20 and then uniformly push the model arch out of the guide. These pins or pushers can further serve for anchoring the model to the base plate when these pins, during the hardening of the model material, project beyond the upper edge of the bores into which the pins are inserted. Each threaded pin then forms the thread in the model material during the hardening process.

Preferably threaded pins, which have cylindrical projections, are screwed into the base plate 1 before the formation of the dental cast as shown in FIG. 11, and the bores which are not necessary any longer are closed with plastic mass or wax. If these self-cutting threaded pins are inserted into the base plate deeply the free front surfaces of the pins can be flush with the upper base surface of plate 1. Then only minimal rotations of the pins are later necessary in order to release friction between the model and the base plate.

Figure 13:
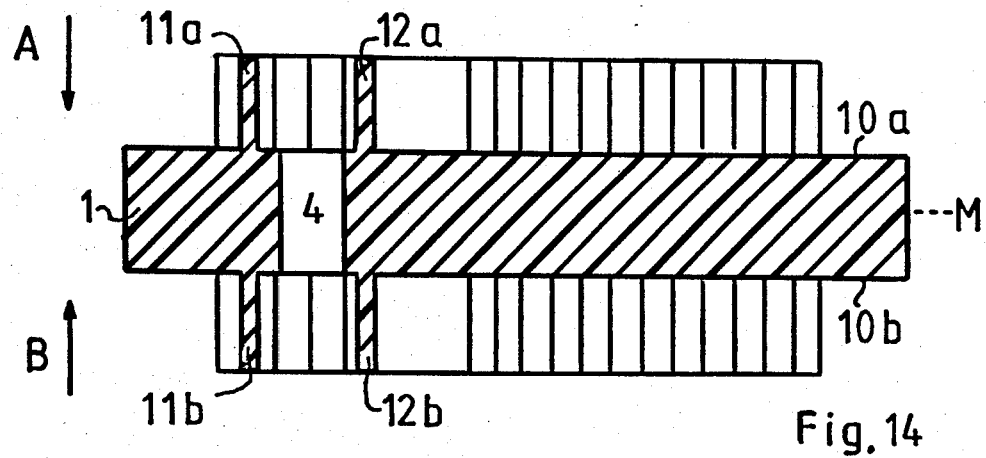
FIGS. 13a and 13b illustrate the upper side and the lower side of the base plate of yet another modification.
Figure 14:
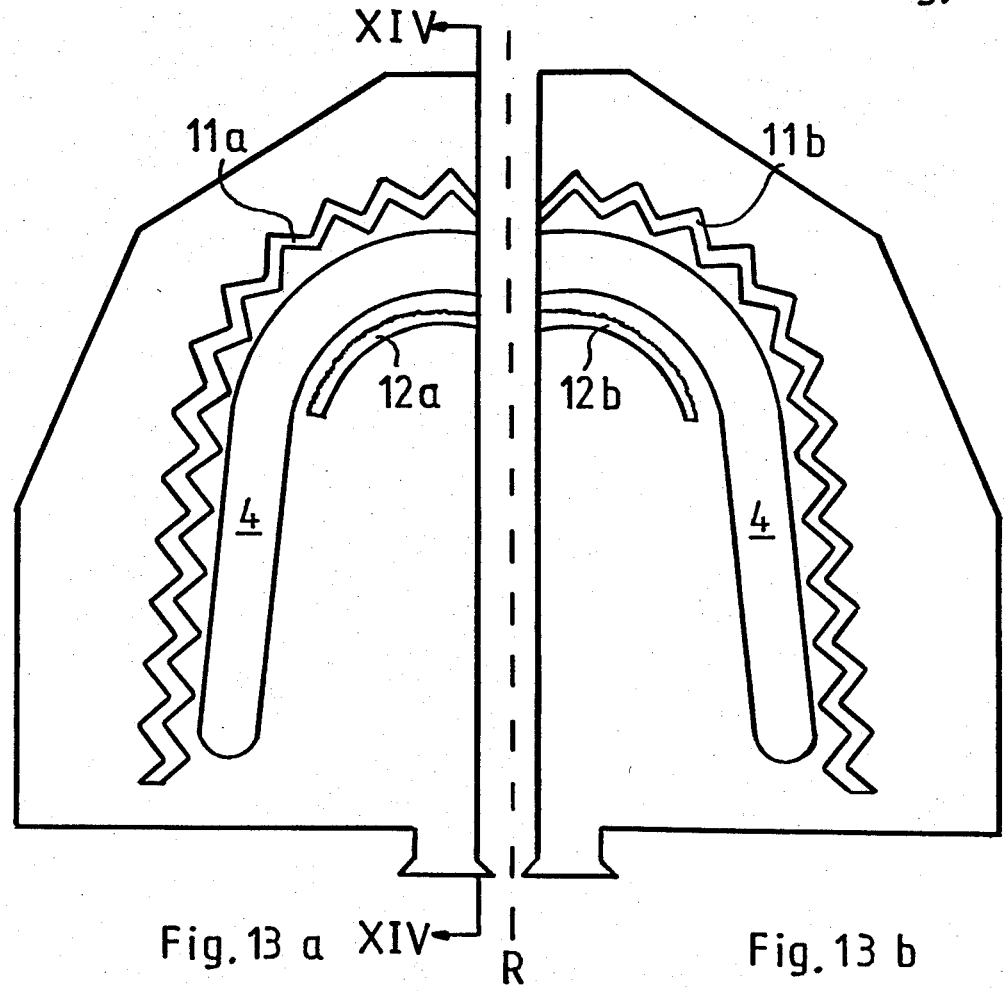
FIG. 14 is a sectional view taken along line XIV—XIV of FIG. 13.

With reference to FIGS. 13 and 14 the illustrated embodiment of the invention has only one half of the tooth arch fixed on the base plate 1. FIG. 13a depicts a view seen from arrow A of FIG. 14, whereas FIG. 13b shows a view seen in the direction of arrow B in FIG. 14. The base plate 1 has an imaginary central plane M which extends parallel to the upper base surface 10a. The base plate has an upwardly projected ridge 11a and a ridge 11b projected downwardly with respect to the central plane M. Both ridges superimpose one another. Furthermore, on the palate side of the plate two side walls 12a and 12b are respectively formed as one-piece with plate 1 on the upper face 10a and lower face 10b. The symmetry of the structure is defined in perforation 4. Such a base plate structure results when, for example both halves of the base plate according to FIG. 1 are turned about the rotation axis R relative to each other. As seen from the drawing, the upper side of the plate 1 can be used for fixing the left-hand half of the tooth are and the lower side of the base plate can be utilized for fixing the right-hand half of the tooth arc. It is also necessary to use only one individual base plate which is universal. Thereby ridge 11, which lies opposite to a corresponding model and serves for securing the base plate in an articulator, can replace split cast ribs. The securing of the base plate in the articulator can be carried out in the known fashion by gypsum. Since all the embodiments of the base plate have a similar zigzag-like ridge one can use a casting resin mold with a corresponding zigzag-shaped slot, which is fixed in the articulator. This casing resin mold is fixed at the upper part in one articulator and at the lower part in another articulator. The base plate can be then inserted into the casting resin mold when only a respective model of the opposite jaw is secured by means of gypsum in the articulator in the certain fashion. The ridge of this base plate has two functions. It serves firstly for securing the model on the base plate and secondly it serves for fixing the base plate on the casting resin mold held in the articulator.

The dental model is therefore produced the individual tooth stumps of which are precisely fixed and guided on the base plate. The correct position of the tooth stumps on the base plate is ensured after resetting the tooth stumps by the shape of the zigzag ridge and also by guiding motches and guiding grooves. The working process with the dental model according to the invention is therefore much more economical as compared to conventional methods.

Furthermore, no additional guiding pins are required which also reduces costs of the model.

It will be understood that each of the elements described above, or two or more together, may also find a useful application in other types of dental models differing from the types described above.

While the invention has been illustrated and described as embodied in a dental model, it is not intended to be limited to the details shown, since various r:odifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A dental device for making teeth prothesis portions such as cast fillings, crowns, bridges, dental protheses or the like, comprising in combination a prefabricated base plate; a dental positive tooth impression having tooth stumps and made of a hardenable model material; said tooth stumps being releasably securable on said base plate; and guide means for guiding at least one tooth stump on said base plate, said guide means including at least one guiding wall portion formed on said base plate integrally therewith, said wall portion producing a plurality of respective guiding surfaces immediately on said tooth stump during the hardening of the material of said tooth stumps when the base plate is set on the tooth impression, said base plate being formed with a perforation having side walls, the side walls of said perforation constituting said guiding wall portion and producing said guiding surfaces on said tooth stump, said base plate having a base surface and being formed with a ridge extended outwardly from said base surface and being integral with said base plate, said ridge following an arched path of a dental arch orientation and being inserted into said impression approximately centrally of a tooth stump, said ridge forming a further wall portion also producing said guide surfaces, said perforation at least partially also following an arched path of a dental arch orientation and being radially spaced from said ridge so that the side walls of said perforation and said further wall portion form extensive guide surfaces along the dental arch, said base plate further including at least one lateral projection outwardly extended therefrom and at a distance from said ridge, said projection having an inner face perpendicular to said base plate and being integral with the base plate, said projection also producing said guiding surfaces on said tooth stump during hardening of the model material.

2. The dental device as defined in claim 1, wherein said projection is at least partially interrupted by slots.

3. The dental device as defined in claim 1, wherein said ridge and said projection are formed at two opposite sides from said perforation and near the same.

4. The dental device as defined in claim 1, wherein two said projections are formed on said base plate, said two projections being formed at two opposite sides of said ridge.

5. The dental device as defined in claim 4, wherein one of said projections is partially interrupted by slots to form wall portions spaced from each other in the direction of the tooth arch, said wall portions forming at least some of said guiding surfaces.

6. The dental device as defined in claim 5, wherein at least one of said wall portions is formed with a protrusion extended at the distance from and parallel to said base plate, said tooth stump being formed with at least one recess, said protrusion being engageable and lockable in said recess.

7. The dental device as defined in claim 6, wherein said base plate has a lip-oriented outer side and a palate-oriented inner side, said slots opening towards an edge of said base plate.

8. The dental device as defined in claim 7, wherein said one of said projections is formed on the lip-oriented outer side of the base plate, said one of said projections being elastically pivotable outwardly from a respective guiding surface of said tooth stump.

9. The dental device as defined in claim 8, wherein said base plate is formed with a plurality of bores in the region of said ridge and further including pushers insertable into said bores from the side of the base plate facing away from said tooth impression, said pushers pushing the tooth impression out from said guiding wall portion.

10. The dental device as defined in claim 9, wherein said pushers are threaded pins which also serve for fixing the tooth stump to the base plate.

11. The dental device as defined in claim 1 wherein said base plate is formed of synthetic plastic material by injection molding.

12. The dental device as defined in claim 11, wherein said perforation has a contour of a tooth arch.

13. The dental model as defined in claim 12, wherein said ridge extends perpendicular to the base surface of said base plate.

14. The dental device as defined in claim 13 wherein said base plate has a lip-oriented outer side and a palate-oriented inner side, said ridge being formed at the lip-oriented side relative to said perforation and said projection being formed at the palate-oriented side relative to said projection, said ridge extending on said plate over the entire teeth area, said projection extending on said plate over the area of the front teeth.

15. The dental device as defined in claim 14, wherein the side walls forming said perforation are at least partially toothed.

16. The dental device as defined in claim 14, wherein said ridge forming said further wall portion is at least partially toothed.

17. The dental device as defined in claim 16, wherein said ridge is at least partially zigzag-shaped.

18. The dental device as defined in claim 14, wherein said projection is at least partially toothed.

19. The dental device as defined in claim 18, wherein said projection has an inner surface and is provided with a plurality of guiding grooves in said inner surface, said projection further having an upper surface and being provided with a plurality of guiding notches in said upper surface, said guiding grooves merging into said guiding notches.

20. The dental device as defined in claim 14, wherein said at least one wall portion, said ridge and said projection, which produce said guiding surfaces on said tooth stump, extend parallel to each other and normally to said base plate.

21. The dental device as defined in claim 20, wherein said ridge has a cross-section which is gradually decreased towards said tooth stump.

22. The dental device as defined in claim 14, wherein said perforation is subdivided into a plurality of chambers by a plurality of ribs which extend transversal of said perforation.

23. The dental device as defined in claim 14, wherein said base plate is provided with a bottom plate which closes said perforation from beneath, said bottom plate having abutments extended into said perforation, the cross-section of said abutments corresponding to the cross-section of said perforation.

24. The dental device as defined in claim 23, wherein said abutments extend into said perforation up to the base surface of the base plate and fill said perforation entirely.

25. The dental model as defined in claim 23, wherein said abutments only partially fill said perforation.

26. The dental device as defined in claim 23, wherein said bottom plate is connected to said base plate in a force-locking manner.

27. The dental device as defined claim 23, wherein said bottom plate is connected to said base plate in a form-locking manner.

28. The dental device as defined in claim 27, further including threaded pins for connecting said base plate to said bottom plate, said pins being insertable from a lateral side of the base plate into said abutments.

29. The dental device as defined in claim 28, wherein said abutments have free front faces which are polished.

30. The dental device as defined in claim 27, wherein said bottom plate is made out of thermoplastic material by injection molding as a one-piece.

31. The dental device as defined in claim 27, wherein said bottom plate is made out of glass.

32. The dental device as defined in claim 27, wherein said bottom plate is made out of metal.

33. The dental device as defined in claim 14, wherein said base plate has a further base surface opposite to the aforementioned base surface, said wall portion and said further wall portion both extending from said aforementioned base surface and said further base surface.

34. The dental device as defined in claim 33, wherein said base plate has a central plane, said aforementioned base surface and said further base surface being parallel to and symmetrical relative to said central plane.

35. The dental device as defined in claim 34, wherein said base plate has a polygonal contour.

36. The dental device as defined in claim 35, wherein the base plate has a quadrant-shape periphery.

37. The dental device as defined in claim 1, wherein said base plate has a polygonal contour.

38. The dental device as defined in claim 1, wherein said at least one wall portion and said further wall portion extend perpendicular to the base plate whereby the guiding surfaces on said tooth stump formed by said wall portions are parallel to each other.

39. The dental device as defined in claim 1, wherein said tooth stump is provided with a reinforcement unreleasably imbedded therein, said reinforcement surrounding said ridge at two lateral sides thereof, said reinforcement including a slide with two arms which engage said ridge, and a projection extended outwardly from said arms, said slide having an outer surface which is knurled.

40. The dental device as defined in claim 39, wherein said model material is hardenable gypsum.

41. The dental device as defined in claim 1, wherein said model material is plastics.

42. The dental device as defined in claim 41, wherein said material is epoxy plastics.

43. The dental device as defined in claim 41, wherein said material is epimin plastics.

44. The dental device as defined in claim 1, wherein said base plate is provided with a bottom plate which closes said perforation from beneath.

45. The dental device as defined in claim 1, said base plate having a palate side and a lip side, said wall portion being formed on said palate side.

* * * * *